United States Patent
Strickler et al.

(12)

(10) Patent No.: US 6,211,419 B1
(45) Date of Patent: Apr. 3, 2001

(54) PROCESS FOR THE PREPARATION OF ALKYLENE GLYCOLS

(75) Inventors: Gary R. Strickler; Von G. Landon; Guo-Shuh John Lee, all of Midland, MI (US)

(73) Assignee: The Dow Chemical Company, Midland, MI (US)

( * ) Notice: Subject to any disclaimer, the term of this patent is extended or adjusted under 35 U.S.C. 154(b) by 0 days.

(21) Appl. No.: 09/557,526

(22) Filed: Apr. 24, 2000

(51) Int. Cl.$^7$ .................................................. C07C 27/00
(52) U.S. Cl. ......................... 568/867; 568/811; 568/881; 568/833
(58) Field of Search .................................. 568/867, 811, 568/881, 833

(56) References Cited

U.S. PATENT DOCUMENTS

| 4,277,632 | * | 7/1981 | Kumazawa et al. | 568/867 |
| 4,701,632 | * | 10/1987 | Soo et al. | 568/867 |
| 5,488,184 | * | 1/1996 | Reman et al. | 568/867 |

FOREIGN PATENT DOCUMENTS

| 57-139026 | * | 8/1982 | (JP) | C07C/29/10 |
| 2001901 | * | 5/1992 | (RU) | C07C/29/10 |
| 2002726 | * | 5/1992 | (RU) | C07C/29/10 |
| 95/20559 | * | 8/1995 | (WO) | C07C/29/10 |
| 97/33850 | * | 9/1997 | (WO) | C07C/29/10 |
| 99/31033 | * | 6/1999 | (WO) | C07C/29/10 |
| 99/31034 | * | 6/1999 | (WO) | C07C/29/10 |

* cited by examiner

Primary Examiner—Johann Richter
Assistant Examiner—Elvis O. Price
(74) Attorney, Agent, or Firm—Elisabeth T. Jozwiak

(57) ABSTRACT

A method for operating an epoxide containing system which contains a catalyst is disclosed. The method comprises feeding carbon dioxide to the epoxide containing system at an amount of from 0.01 to 5.0 weight percent; and maintaining the epoxide containing system at a temperature of from 100° C. to 150° C. The catalyst has a half life of at least 40 days at 120° C. The present invention allows anion exchange resins in the bicarbonate form to be used for the hydrolysis of ethylene oxide at temperatures exceeding 100° C. The rate of catalyst swelling is minimized and lifetime of the catalyst enhanced.

10 Claims, No Drawings

PROCESS FOR THE PREPARATION OF ALKYLENE GLYCOLS

FIELD OF THE INVENTION

This invention relates to the preservation of catalysts in epoxide-containing systems. More particularly, the present invention relates to catalyst preservation in the preparation of ethylene glycol.

BACKGROUND OF THE INVENTION

Alkylene glycols, such as ethylene glycol and propylene glycol, are widely used as raw materials in the production of polyesters, polyethers, antifreeze, solution surfactants, and as solvents and base materials in the production of polyethylene terephthalates (e.g. for fibers or bottles). Commercial processes for the preparation of alkylene glycols typically involve the liquid phase hydration of the corresponding epoxide in the presence of a large molar excess of water (see, e.g., Kirk-Othmer, *Encyclopedia of Chemical Technology*, Vol. 11, Third Edition, page 929 (1980)).

Ethylene glycol is commonly produced by the noncatalytic reaction of ethylene oxide and water. The reactions are run adiabatically, and the heat of reaction is absorbed by the reacting fluids which respond with an increase in temperature. The reaction temperature is typically 120° C. at the inlet to the reactor and often exceeds 180° C. at the exit point.

High temperatures are desirable in the preparation of ethylene glycol because the rate of reaction is maximized and selectivity is unaffected by high temperature. An added advantage of high temperature operation is that it reduces the need to supply external sources of heat to downstream purification equipment for the separation and recovery of unreacted water from the ethylene glycol product.

High ratios of water to ethylene oxide are typically fed to the commercial reactors to favor the production of mono-ethylene glycol, which is capable of also reacting with ethylene oxide to form diethylene glycol. Additionally, the diethylene glycol can react with ethylene oxide to form triethylene glycol, and so forth.

Formation of higher glycols is viewed as commercially unattractive, since the production of these higher glycols consumes valuable ethylene oxide, and markets for use of higher glycols are limited. The use of excessive quantities of water to favor mono-ethylene glycol add to the cost of manufacture because the excess water must be removed with energy through capital intensive evaporation and distillation process steps.

Catalytic systems have recently been studied for the purpose of selectively hydrolyzing epoxides, although commercialization has been an elusive goal. For example, JP 57-139026 teaches a catalyzed process utilizing anion exchange resins in the chloride form and carbon dioxide resulting in superior selectivity over comparable non-catalyzed or thermal processes. One drawback to the process taught in JP is the formation of ethylene carbonate, separation of which is difficult and expensive.

Examples of catalytic processes are also taught in RU 2001901 and RU 2002726. Therein are taught processes for converting a catalyst to the bicarbonate form before the catalytic reaction, and reducing the concentration of carbon dioxide to as low as 0.01 percent by weight in order to allow the catalyst to be more selective toward monoethylene glycol.

U.S. Pat. No. 5,488,184 (the '184 Patent) also teaches a catalytic process wherein carbon dioxide is reduced or eliminated from the reaction mixture in order to enable higher reaction rates. The '184 Patent teaches that, for the bisulfite form of the catalyst, addition of carbon dioxide is beneficial to the reaction selectivity, but that for other anion forms of the catalyst, including the bicarbonate and formate forms, addition of carbon dioxide is detrimental to selectivity as well as the reaction kinetics for the bicarbonate form. The '184 Patent thus teaches that the concentration of carbon dioxide be kept below 0.1 wt %. The '184 Patent also teaches using relatively low reaction temperatures of around 80° C. Such low reaction temperatures require external cooling to maintain.

PCT publications WO 99/31034 and WO 99/31033 also teach catalytic processes at relatively low reaction temperatures. Such references teach advantageously using a specific reactor design and adjusting the pH, respectively, to prolong the catalyst lifetime and minimize catalyst swelling.

The aforementioned references are limited by low reaction temperature, due primarily to the fact that anion exchange resins in the bicarbonate form, if exposed to high temperatures, typically deactivate quickly, as quickly as a few days when temperatures exceed 120° C. Because the hydrolysis reaction is exothermic, even higher reaction temperatures would be desired to permit maximum temperature rise without cooling.

Commercialization of catalytic processes require that the catalyst be stable for an extended period of time. Otherwise, plant shut-downs to remove the catalyst from the reactor result in added expense and significant economic disadvantage.

Thus a catalytic system is desired that provides a combination of long catalyst life with minimal physical and chemical changes while operating at high temperature with efficient use of energy.

SUMMARY OF THE INVENTION

In one aspect, the present invention is a method for operating an epoxide containing system which comprises a catalyst. The method comprises feeding carbon dioxide to the epoxide containing system at an amount of from 0.01 to 5.0 weight percent; and maintaining the epoxide containing system at a temperature of from 100° C. to 150° C. The catalyst has a half life of at least 40 days at 120° C.

In another aspect, the present invention is a method for making an alkylene glycol comprising feeding an alkylene oxide and water to a reaction zone, the reaction zone comprising a catalyst; feeding carbon dioxide to the reaction zone; and maintaining a temperature of at least 100° C. in the reaction zone. The catalyst has a half-life of at least 40 days at 120° C.

In yet another aspect, the present invention is a method for making an alkylene glycol comprising feeding an alkylene oxide and water to at least one adiabatic reactor, the reactor comprising a catalyst; feeding carbon dioxide to the reactor; and maintaining a temperature of at least 100° C. in the reactor. The catalyst has a half-life of at least 40 days at 120° C.

One advantage of the present invention is that it allows anion exchange resins in the bicarbonate form to be used for the hydrolysis of ethylene oxide at temperatures exceeding 100° C. A further advantage of the present invention is that the rate of swelling is minimized and lifetime of the catalyst enhanced. Surprisingly, these advantages are observed, despite the fact that the prior art recited above taught away from adding substantial quantities of carbon dioxide to such epoxide containing systems.

DETAILED DESCRIPTION OF THE INVENTION

This invention is a method for making glycols from epoxides and water and a method for operating such epoxide-containing systems. The preferred epoxides include ethylene oxide (EO), propylene oxide (PO), and butylene oxide (BO), and the preferred alkylene glycols include their respective monoalkylene glycols: ethylene glycol (EG), propylene glycol (PG), and butylene glycol (BG). Most preferably, this invention is a process for preparing monoethylene glycol from ethylene oxide and water.

The first step of the method of the present invention comprises feeding water and an epoxide to a reaction zone. The reaction zone preferably comprises at least one adiabatic reactor containing a catalyst bed. The term "adiabatic reactor" is defined as a reactor having substantially no heat removed therefrom. In an adiabatic reactor, the temperature rise can be controlled by feeding a large excess of water to allow the heat to be absorbed by the water feed. The adiabatic reactor is usually a cylindrical vessel or series of vessels with no heat transfer between vessels, operated in plug flow manner to obtain maximum monoglycol selectivity.

The reaction zone is desirably maintained under conditions such that the epoxide and the water react to form a glycol product stream comprising glycol and water. For purposes of this invention, the "glycol product stream" shall be read broadly to include any product stream exiting a reactor which contains at least glycol and water. The glycol product is generally in mixture, solution, or contained within unreacted water.

In light of the disclosure herein, conditions which are conducive for the reaction to occur are within the skill in the art. Factors for consideration include the optimum temperature, pressure, and water to alkylene oxide ratio for reacting the feed stream(s) without providing conditions which significantly degrade the catalyst bed or selectivity to the desired product.

One of the conditions conducive to reacting the epoxide and water to form a glycol product stream is temperature. As set forth herein above, high temperatures are desirable in the preparation of glycol because the rate of reaction is maximized, and the amount of unreacted water is reduced. The reaction temperature in a catalytic reactor is at least 100° C. Preferably, a temperature of at least 110° C. is maintained, more preferably, a temperature of at least 115° C. is maintained, and even more preferably, a temperature of at least 120° C. is maintained in the catalytic adiabatic reactor. Preferably, the temperature in the catalytic reactor is no more than 150° C., more preferably no more than 145° C., even more preferably no more than 140° C. and still even more preferably no more than 135° C.

The reaction pressures are generally in the range of about 100 kPa to about 10000 kPa, preferably 500 kPa to about 5000 kPa, with the intent to maintain reactants in the liquid phase.

As set forth herein above, a catalyst bed must be included in at least one adiabatic reactor in the reaction zone. Typically the catalyst bed is a fixed catalyst bed, but it may be a fluidized bed, a moving bed, or a slurry. It is desirable to minimize the volume of liquid in the catalyst bed to reduce the required reactor volume and to minimize noncatalytic reactions which may lead to lower monoglycol selectivity. Thus, a fixed bed is preferred over other types of catalyst beds.

The catalyst bed may comprise any material capable of catalyzing the desired reaction in the adiabatic reactor in which it is employed. It should be of such a nature as to allow reactants and products to pass through the bed, yet provide a sufficient surface area for catalytic contact. Desirably, the catalytic material is solid and is insoluble in either the reactants or the glycol products under the conditions in the process.

Preferably, the catalyst for this invention is an anion exchange resin. In light of the disclosure herein, selection of a suitable anion exchange resin is within the skill in the art. Preferably, such anion exchange resin is a bicarbonate-type anionic exchange resin. Illustrative of bicarbonate-type exchange resins are the disclosures of WO 95/20559, WO 97/33850, RU Patent Nos. 2002726 and 2001901 (each of which is incorporated herein by reference). It is particularly preferred that the anion exchange resins contain quaternary ammonium groups. Examples of suitable, commercially available, anion exchange resins include: Amberlite™ IRA 400 and 900 series (based on polystyrene resins, cross-linked with divinylbenzene) (Rohm and Haas); Lewatit™ M 500 WS (Bayer); Duolite™ A 368, A-101D, ES-131 and A-161 (Rohm and Haas); DOWEX™ MSA-1, MARATHON A, and MARATHON MSA; and DIAION™ XSA1000 (Mitsubishi). Anion exchange resins with trimethyl benzyl ammonium groups (i.e., Type I resins) are particularly preferred for this invention.

The second step of the method includes feeding carbon dioxide to the reaction zone in an amount of at least 0.01 weight percent based on the weight of the total feed. Preferably, carbon dioxide is fed to the reaction zone in an amount of at least about 0.05 weight percent, more preferably, in an amount of at least 0.1 weight percent. The amount of carbon dioxide fed to the reaction zone preferably does not exceed 5.0 weight percent, more preferably does not exceed 3.0 weight percent, even more preferably does not exceed 2.0 weight percent, and still even more preferably does not exceed 1.0 weight percent, since excessive amounts of carbon dioxide could adversely impact the rate of hydrolysis, conversion and selectivity. Preferably, carbon dioxide is added in a sufficient amount to provide a pH of between 2.0 and 8.0, more preferably between 3.0 and 7.0, and even more preferably between 3.5 and 6.0.

The method of the present invention also includes the step of removing or replacing the catalyst at a certain minimum frequency. Because a catalyst normally loses its activity over a certain period of time, the catalyst must be removed and/or replaced in order for the operation to continue. The level of carbon dioxide added to the system directly affects catalyst degradation and lifetime. Preferably, the catalyst must be removed or replaced at a frequency of less than every 1 year, more preferably less than 1½ years and even more preferably less than 2 years. Catalyst degradation can be represented by catalyst half-life, which is defined as being the amount of time required for the catalyst to lose half of its catalytic activity. Preferably, the half-life of the catalyst used in the present invention is increased by at least 20 days relative to operation without carbon dioxide, more preferably the half-life is increased by at least 40 days, and even more preferably the half-life is increased by at least 60 days. Preferably, at an operating temperature of 120° C., the catalyst half-life is at least 40 days.

The method of the present invention also reduces the amount of swelling that the catalyst must undergo. Preferably, using the method of the present invention, the rate of continuous, unlimited swelling is reduced by at least 50% relative to operation without the addition of carbon dioxide, more preferably at least about 60%, and even more preferably at least about 70%. Thus, for example, if the rate of continuous catalyst swelling is 1.0% per day using an operation without $CO_2$ addition, then the rate of continuous swelling using an adiabatic reactor is preferably reduced to 0.5% or less per day.

Of course, the catalyst half-life and the rate of catalyst swelling will depend upon the specific catalyst. More swelling can be tolerated with a catalyst having a higher activity. Preferably the rate of catalyst swelling is reduced to less than 1% per day, more preferably less than 0.5% per day, and even more preferably less than 0.1% per day.

For the practice of this invention, water of different purity may be used such as fresh water, deionized water, steam distilled water, condensate water (which may contain some residual glycol compounds), and also recycled water recovered from the dehydration process in the production of alkylene oxide and alkylene glycol (which may contain residual glycol). The water is provided in an amount which is in a stoichiometric excess of that required for forming a desired glycol from reaction with epoxide. Preferably, the molar feed ratio of water to epoxide is at least about 1.1, more preferably at least about 2.0, and even more preferably at least about 5.0. Preferably, the molar feed ratio is no more than about 50, more preferably no more than about 30, and even more preferably no more than about 20. Those of skill in the art will recognize that this ratio will vary depending upon the epoxides employed, the reaction conditions, and the specific catalyst utilized.

The epoxide used in the present invention can be unfinished epoxide containing small levels of impurities such as, for example, aldehydes, or the epoxide can be pure epoxide. The water and epoxide feed may be fed to the reaction zone separately or together as co-feed. The water and epoxide may be fed to the reactors as a gas, as a liquid, or as a combination thereof.

EXAMPLES

Each of the following examples was run in the reactor described below. All catalysts were prepared, reactants fed, and samples analyzed according to the procedures below. Conditions were identical except where noted.

Description of the Reactor

The reactor was a jacketed, 1.1 cm inner diameter, 23 cm long, 316 Stainless Steel tube. Heat transfer fluid was circulated through the jacket to maintain a constant, uniform reaction temperature. A 3.2 mm outer diameter thermocouple with six evenly spaced junctions was mounted concentrically inside the tube to measure the reaction temperature. The tube was packed with 15 ml of the resin catalyst. Aqueous and ethylene oxide feed streams were pumped at constant flow rates, mixed, and fed to the reactor. The reactor was operated at 12 bar to avoid vapor formation.

Preparation of the Catalyst

The ion exchange resin used in the examples was DOWEX™ Marathon A, chloride anion form, with an exchange capacity of 1.3 milliequivalents per milliliter of wet resin. The chloride form of the resin was converted to the bicarbonate form by reacting it with aqueous $NaHCO_3$ for use in the examples.

Feed Solution

The ethylene oxide feed was 99.9% pure with an unknown amount of $CO_2$, and the feed rate was 8.0 g/h. The aqueous feed was 64 g/h of deionized, $CO_2$-free water (18 MΩ resistance, pH 7.0).

Analytical and Calculations:

The products were analyzed by gas chromatography for ethylene oxide (EO), mono-ethylene glycol (MEG), diethylene glycol (DEG), and triethylene glycol (TEG). The GC contained a capillary column and a flame ionization detector.

The conversion in the reactor was calculated by determining the moles reacted and dividing by the moles fed and converting to a percentage basis.

The selectivity for each product was calculated by determining the number of moles of ethylene oxide that was consumed when converting to a specified product and dividing by the number of moles of ethylene oxide that was consumed during reaction and expressing on a percentage basis.

The peak temperature was the highest temperature recorded by the six thermocouples inside the catalyst bed.

The swelling rate was calculated as the increase in catalyst volume divided by the volume of catalyst loaded into the reactor expressed on percentage per day basis.

The half-life is the amount of time required for the catalyst to lose half of its catalytic activity.

Comparative Example 1

Operation at 105° C. Without Any Additives

The reaction was run according to the aforementioned procedure and allowed to run for 32 days. During the course of the reaction, the EO conversion and MEG selectivity were closely monitored and at the end of the run determined to be 99.7% and 97.6%, respectively. The half-life of the catalyst was 27 days. After shutting down the reactor, the volume of catalyst removed was measured. It was determined that the catalyst had swollen to 25 ml from the original 15 ml. This represented a swelling rate of 2.1% per day. Results for the run are shown in Table 1.

Comparative Example 2

Operation at 125° C. Without Any Additives

To demonstrate the effects of running at higher temperature on swelling an experiment was run following the procedure of example 1. In this example, the reactor jacket temperature was set to control at 125° C. and the peak temperature reached 133° C.

The reaction was allowed to run for 3 days. During the course of the reaction, the conversion and selectivity were closely monitored and at the end of the run determined to be 99.98% and 89.3% respectively. The reactor over-pressured on the third day. The half-life of the catalyst was determined to be 13 days . The reactor was shut down and the catalyst was removed. It was discovered that the catalyst had swelled and plugged off the reactor. The volume of catalyst removed from the reactor was 25.5 ml. It was determined that the catalyst was swelling 17.5% per day. Results for the run are shown in Table I.

Example 3

Operation at 115° C. With 0.014% $CO_2$

To demonstrate the beneficial effects of adding $CO_2$ to retard swelling an experiment was run following the procedure of example 1. In this example 0.014 weight percent $CO_2$ was co-fed with ethylene oxide and water and the reactor jacket temperature was set to control at 115° C., and the peak temperature reached 124° C.

The reaction was allowed to run for 25 days. The conversion and selectivity at the end of the run were 97.5% and 98.0% respectively. The half-life of the catalyst was 47 days. After 25 days on line, the reactor was shut down and the catalyst was removed. It was determined that the catalyst had swelled but at slower rate than measured during the experiments where $CO_2$ was not added. The volume of catalyst removed from the reactor was 21 ml. It was determined that the catalyst was swelling 1.32% per day. Results for the run are shown in Table I.

Example 4

Operation at 115° C. With 0.14% $CO_2$

To further demonstrate the beneficial effects of adding $CO_2$ to retard swelling an experiment was run following the procedure of example 3. In this example 0.14 weight per cent $CO_2$ was co-fed with ethylene oxide and water. The peak temperature reached 123° C.

The reaction was allowed to run for 47 days. The conversion and selectivity at the end of the run were 78.9% and 97.8% respectively. The half-life of the catalyst was 123 days. After 47 days on line, the reactor was shut down and the catalyst was removed. The volume of catalyst removed from the reactor was 18 ml. It was determined that the catalyst was swelling 0.44% per day. Results for the run are shown in Table I, example 4.

Example 5

Operation at 125° C. With 0.14% $CO_2$

To determine the limits of the beneficial effects of adding $CO_2$ to retard swelling, an experiment was run following the procedure of example 4. In this example, the reactor jacket temperature was set to control at 125° C. and the peak temperature reached 132° C.

The reaction was allowed to run for 38 days. The conversion and selectivity at the end of the run were 91.7% and 97.3%, respectively. The half-life of the catalyst was 59 days. After 38 days on line, the reactor was shut down and the catalyst was removed. The volume of catalyst removed from the reactor was 20.5 ml. It was determined that the catalyst was swelling 0.95% per day. Results for the run are shown in Table I.

TABLE 1

Experimental Results

| Example | Setpoint Temp (° C.) | Peak Temp (° C.) | Run Time (days) | % CO2 Added | Half-life (days) | Swelling (%/day) | Conv (%) | Sel. (%) |
|---|---|---|---|---|---|---|---|---|
| 1 (Comparative) | 105 | 117 | 32 | none | 27 | 2.1 | 99.7 | 97.6 |
| 2 (Comparative) | 125 | 133 | 3 | none | 13 | 17.5 | 99.98 | 89.3 |
| 3 | 115 | 124 | 25 | 0.014% | 47 | 1.32 | 97.5 | 98.0 |
| 4 | 115 | 123 | 47 | 0.14% | 123 | 0.44 | 78.9 | 97.8 |
| 5 | 125 | 132 | 38 | 0.14% | 59 | 0.95 | 91.7 | 97.3 |

What is claimed is:

1. A method for making an alkylene glycol comprising:

feeding an alkylene oxide and water to a reaction zone, the reaction zone comprising a catalyst;

feeding carbon dioxide to the reaction zone in an amount of at least 0.1 weight percent; and maintaining a temperature of at least 100° C. in the reaction zone; wherein the catalyst has a half-life of at least 40 days at 120° C.

2. The method of claim 1 wherein the catalyst comprises an anion exchange resin in the bicarbonate form.

3. The method of claim 1 wherein the alkylene glycol is ethylene glycol, propylene glycol or butylene glycol, and the alkylene oxide is ethylene oxide, propylene oxide or butylene oxide.

4. The method of claim 1 wherein the catalyst undergoes swelling in an amount that is less than 1.0% per day.

5. The method of claim 1 wherein the reaction zone comprises at least one adiabatic reactor.

6. A method for making an alkylene glycol comprising:

feeding an alkylene oxide and water to at least one adiabatic reactor, the reactor comprising a catalyst;

feeding carbon dioxide to the reactor in an amount of at least 0.1 weight percent; and maintaining a temperature of at least 100° C. in the reactor; wherein the catalyst has a half-life of at least 40 days at 120° C.

7. The method of claim 6 wherein the alkylene glycol is ethylene glycol, propylene glycol or butylene glycol, and the alkylene oxide is ethylene oxide, propylene oxide or butylene oxide.

8. The method of claim 6 wherein the catalyst undergoes swelling in an amount that is less than 1.0% per day.

9. The method of claim 1 wherein the carbon dioxide is fed to the reactor in an amount of at least 0.14 weight percent.

10. The method of claim 6 wherein the carbon dioxide is fed to the reactor in an amount of at least 0.14 weight percent.

* * * * *